United States Patent [19]

Oaks et al.

[11] Patent Number: 5,207,225
[45] Date of Patent: May 4, 1993

[54] TRANSESOPHAGEAL ULTRASONIC SCANHEAD

[75] Inventors: Frank B. Oaks, Kent; Perry W. Kaminski, Seattle; Eugene A. Larson, Kirkland, all of Wash.

[73] Assignee: Advanced Technology Laboratories, Inc., Bothell, Wash.

[21] Appl. No.: 762,975

[22] Filed: Sep. 20, 1991

Related U.S. Application Data

[63] Continuation-in-part of Ser. No. 613,338, Nov. 14, 1990, Pat. No. 5,050,610.

[51] Int. Cl.⁵ .............................. A61B 8/12
[52] U.S. Cl. ................ 128/660.1; 128/660.07; 128/661.01; 128/662.06
[58] Field of Search ............ 128/660.07, 660.08, 128/660.09, 660.1, 662.06, 661.01; 73/623, 634

[56] References Cited

U.S. PATENT DOCUMENTS

| | | | |
|---|---|---|---|
| 4,398,422 | 8/1983 | Haerten | 128/660.08 |
| 4,501,277 | 2/1985 | Hongo | 128/660.07 |
| 4,541,435 | 9/1985 | Saito et al. | 128/660.07 |
| 4,637,256 | 1/1987 | Sugiyama et al. | 128/660.09 |
| 4,722,345 | 2/1988 | Ueno et al. | 128/660.09 |
| 4,817,616 | 4/1989 | Goldstein | 128/662.06 |
| 4,880,011 | 11/1989 | Imade et al. | 128/662.06 |
| 4,932,414 | 6/1990 | Coleman et al. | 128/660.09 |
| 5,054,492 | 10/1991 | Scribner et al. | 128/662.06 |
| 5,099,850 | 3/1992 | Matsui et al. | 128/662.06 |

FOREIGN PATENT DOCUMENTS

| | | | |
|---|---|---|---|
| 0139574 | 6/1985 | European Pat. Off. | 128/660.1 |
| 3727213A1 | 2/1988 | Fed. Rep. of Germany | 128/660.1 |

OTHER PUBLICATIONS

Hanrath, P. et al. "Transesophageal Horizontal and Sagittal Imaging of The Heart With a Phased Array System. Initial Clinical Results"; dated 1982, pp. 280-288.

Primary Examiner—Kyle L. Howell
Assistant Examiner—George Manuel
Attorney, Agent, or Firm—W. Brinton Yorks, Jr.

[57] ABSTRACT

An ultrasonic transesophageal scanhead is provided which enables a physician to easily and quickly change the orientation of the image plane during a scanning procedure. Means are provided on either the scanhead or the ultrasound system for selecting the imaging plane. As the imaging plane selector is actuated, an indication of the orientation of the selected plane appears concurrently on the monitor of the system along with a display of ultrasonic information of the selected plane. In a preferred embodiment the indication of the selected plane is displayed both graphically and numerically. A recording of the displayed information will thus capture both the ultrasonic information as well as the image plane orientation. A physician reviewing the recording will thereby know the exact orientation of the image being viewed, leading to a better informed and more precise diagnosis of medical conditions of the body.

29 Claims, 5 Drawing Sheets

TRANSESOPHAGEAL ULTRASONIC SCANHEAD

This is a continuation in part of U.S. patent application Ser. No. 613,338, filed Nov. 14, 1990, now U.S. Pat. No. 5,050,610.

This invention relates to ultrasonic diagnostic systems which utilize ultrasonic transducer scanheads to provide diagnostic information concerning a medical patient and, in particular, to scanheads which may be introduced into a body cavity to perform ultrasonic scanning from within the body.

Ultrasonic diagnostic imaging systems are in widespread use for performing ultrasonic imaging and measurements through the use of scanheads which are placed against the skin. Such scanheads are in common use by radiologists, cardiologists, and obstetricians for examinations of the heart, a developing fetus, or internal abdominal organs. These systems operate by controlling the scanhead to transmit ultrasonic energy through the skin and into the body and receiving ultrasonic echoes returned from the internal structure of the body. Such systems are able to noninvasively provide quick and precise diagnosis of various conditions and disease states inside the body.

However, the heart is one organ for which ultrasonic diagnosis has always been difficult. This is because the heart is located in the thoracic cavity, surrounded by the ribs. Ultrasonic scanning through the ribs is not a viable option due to the absorptive and reflective characteristics of bone structure. Accordingly, the accepted clinical procedure is to scan the heart intercostally. But the transmission and reception of ultrasound through the intercostal windows is sometimes not clinically useful, because of acoustic reflections from normal body structures such as the cartilage connected to the ribs.

The advent of endoscopic technology whereby medical devices can be introduced into the body and manipulated external to the body, led to the development of a new technique for ultrasonically scanning the heart: transesophageal echocardiology. By this technique an ultrasonic transducer is located at the end of an elongated probe, which is passed through the patient's mouth and into the esophagus or stomach. From such a position within the thoracic cavity, the ribs no longer pose an impediment to the transmission and reception of ultrasound. The typical transesophageal scanhead includes a control mechanism external to the body, enabling the clinician to manipulate the end of the probe so that the transducer on the probe end is directed as desired toward the heart. This technique, which places the ultrasonic transducer in close proximity to the heart itself, has been found to be most effective in the diagnosis of disease conditions of the heart.

The development of transesophageal echocardiography has resulted in the desire by physicians for two types of images during such a procedure, longitudinal and transverse images. The longitudinal image is a cross-sectional image taken along a longitudinal plane of the heart, and the transverse image is taken along a transverse plane of the heart. Techniques for obtaining these two types of images include the use of two-dimensional arrays of transducer elements which may be electronically selected to form the desired image, and the use of separate transducers, one with a longitudinal orientation and another with a transverse orientation. Through control of the ultrasonic imaging system to which the probe is connected, the clinician can choose one or the other of the two image orientations.

It has been found that a physician often needs to change quickly and easily from one image orientation to the other while retaining all of the diagnostically useful acquired information. Furthermore, the physician or technician performing the diagnostic procedure may not be the diagnosing physician. The person conducting the live examination may have a need to record ultrasonic images for review later by a diagnosing or referring physician. Under such conditions it is often desirable that the recorded images contain not only the ultrasonic image information, but also information concerning the orientation of the recorded images in the body.

In accordance with the principles of the present invention a transesophageal scanhead is provided which enables a physician to easily and quickly change the orientation of the image plane during a scanning procedure. Means are provided on either the scanhead or the ultrasound system for selecting the imaging plane. As the imaging plane selector is actuated, an indication of the orientation of the selected plane appears concurrently on the monitor of the system along with a display of ultrasonic information of the selected plane. In a preferred embodiment the indication of the selected plane is displayed both graphically and numerically. A recording of the displayed information will thus capture both the ultrasonic information as well as the indication of the orientation of the plane being imaged. A physician reviewing the recording will thereby know the exact orientation of the image being viewed, leading to a better informed and more precise diagnosis of medical conditions of the body.

Figure 1:
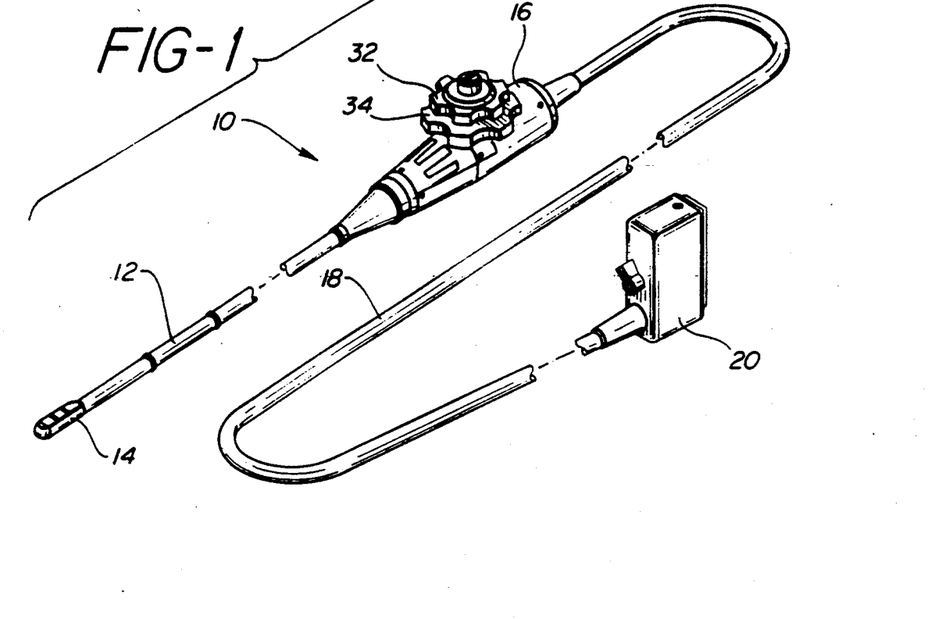
FIG. 1 illustrates a transesophageal scanhead for scanning two orthogonal image planes and constructed in accordance with the principles of the present invention.

Referring first to FIG. 1, a transesophageal scanhead 10 constructed in accordance with the principles of the present invention is shown in perspective. The scanhead includes an elongated tubular probe section 12. The probe section 12 is approximately 100 cm. long and terminates at a distal end 14 on which a pair of ultrasonic transducer arrays are mounted. The probe section 12 contains electrical wires which connect the transducer arrays with a connector 20 at the other end of the scanhead, and stainless steel cables which run to the distal end 14 of the probe and are used to control the orientation of the distal end.

The probe section 12 is connected to the articulating device 16 of the scanhead, which includes two control knobs 32 and 34 for manipulating the distal end of the probe. The control knobs are connected to the cables which extend through the probe section. When knob 32 is turned the distal end 14 of the probe section is moved left and right, and when knob 34 is turned the distal end is moved up and down. The articulating device 16 is connected by a cable 18 enclosing the electrical wiring to a connector 20 which connects the scanhead to an ultrasonic diagnostic system.

Figure 2A:
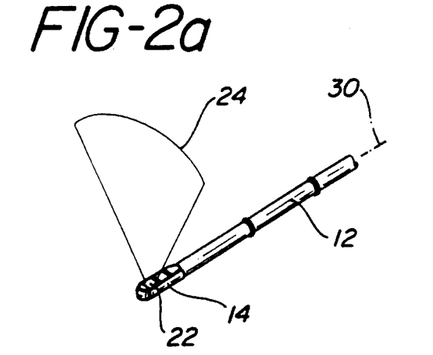
FIGS. 2a and 2b illustrate the image planes scanned by the scanhead of FIG. 1.
Figure 2B:
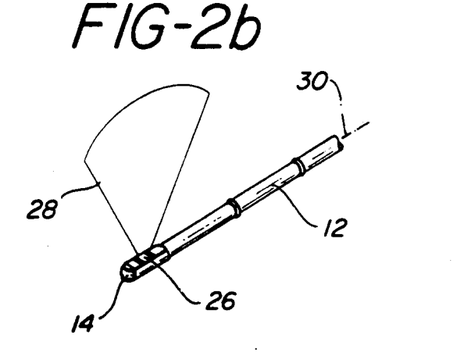

The distal end 14 of the scanhead includes two transducer arrays 22 and 26 which scan the surrounding body during use as shown in FIGS. 2a and 2b. The most distally located transducer array 22 scans a plane 24 of the body which is oriented transversely to the longitudinal axis 30 of the probe section as shown in FIG. 2a. As FIG. 2b shows, when the rearward transducer array 26 is selected, a plane 28 of the body is scanned which is oriented along the longitudinal axis 30 of the probe section. Through selection of the two transducer arrays the clinician is able to scan transverse and longitudinal cross-sectional areas of the heart during use of the scanhead.

Figure 3:
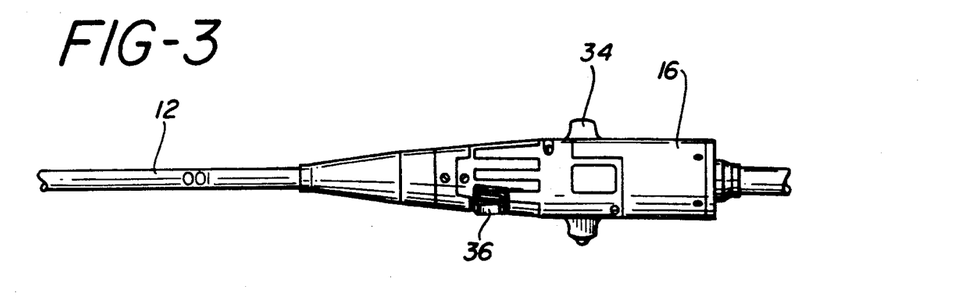
FIG. 3 is a bottom plan view of the control unit of the scanhead of FIG. 1.

FIG. 3 illustrates a bottom plan view of the articulating device 16. Located on the underside of the articulating device is a rocker switch 36. During use of the scanhead at times other than when the distal end of the scanhead is being manipulated, the clinician holds the articulating device with the fingers of a hand cradling the underside of the articulating device. This places the index finger in position to press the rocker switch 36 from one setting to another. As will be described below the scanhead is switched between transverse and longitudinal image planes by pressing the rocker switch 36.

Figure 4:
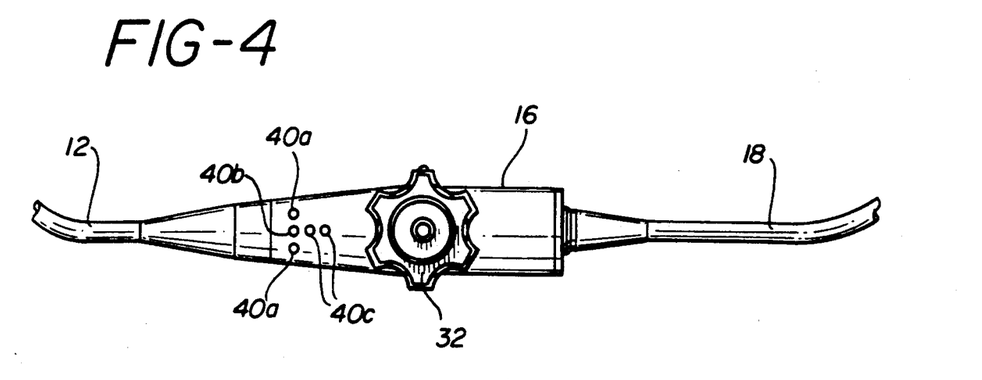
FIG. 4 is a top plan view of the control unit of the scanhead of FIG. 1.

A top plan view of the articulating device 16 is shown in FIG. 4. As this drawing shows, several lights, preferably light emitting diodes (LED's) are located on the upper side of the articulating device 16. Three of the LED's 40a and 40b are arranged in a line transverse to the longitudinal axis of the scanhead, and LED's 40b and 40c are arranged in a line which is parallel to the longitudinal axis. When the articulating device is held by the clinician as described above, appropriate ones of the LED's are illuminated to inform the clinician at a glance as to the orientation of the selected image plane.

Figure 5:
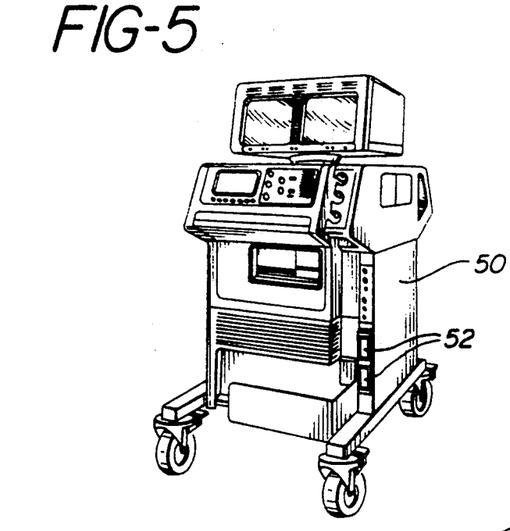
FIGS. 5 and 6 illustrate perspective views of an ultrasonic diagnostic system suitable for use with the scanhead of FIGS. 1-4.
Figure 6:
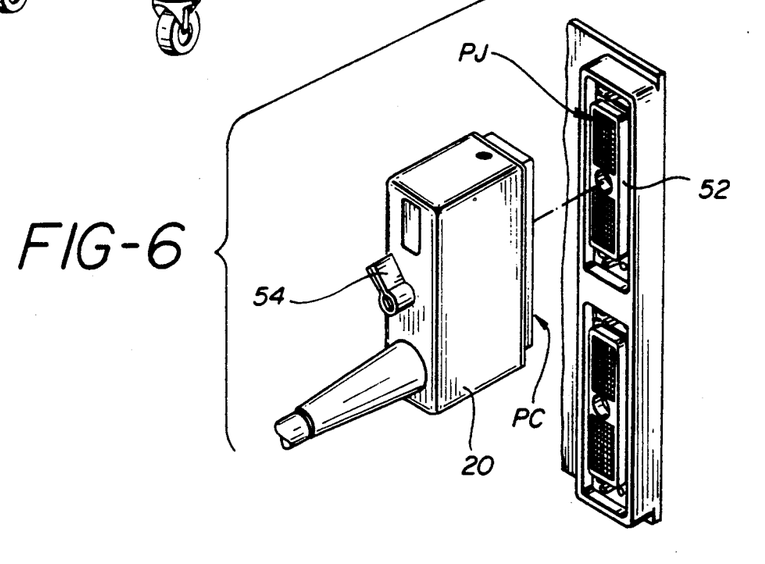

FIG. 5 illustrates a perspective view of an ultrasonic diagnostic system 50 suitable for use with a scanhead of the present invention. The diagnostic system 50 includes monitors on top for viewing ultrasonic data and images formed through processing echo information provided by the transesophageal scanhead 10. The connector 20 of the scanhead is plugged into one of the jacks 52 on the front of the system. The system then provides electrical timing and control signals for the scanhead and processes and displays the returning echo information through adjustment of the controls on the front of the system beneath the monitors. FIG. 6 illustrates in detail the connection of the scanhead connector 20 to one of the system jacks 52. The connector is inserted into the jack, aligning pins in the connector (indicated by the arrow PC) with pins in the jack (indicated by arrow PJ). When the key 54 on the connector is turned the pins in the jack and the connector are mated together and the connector is locked in place in the jack.

Figure 7A:
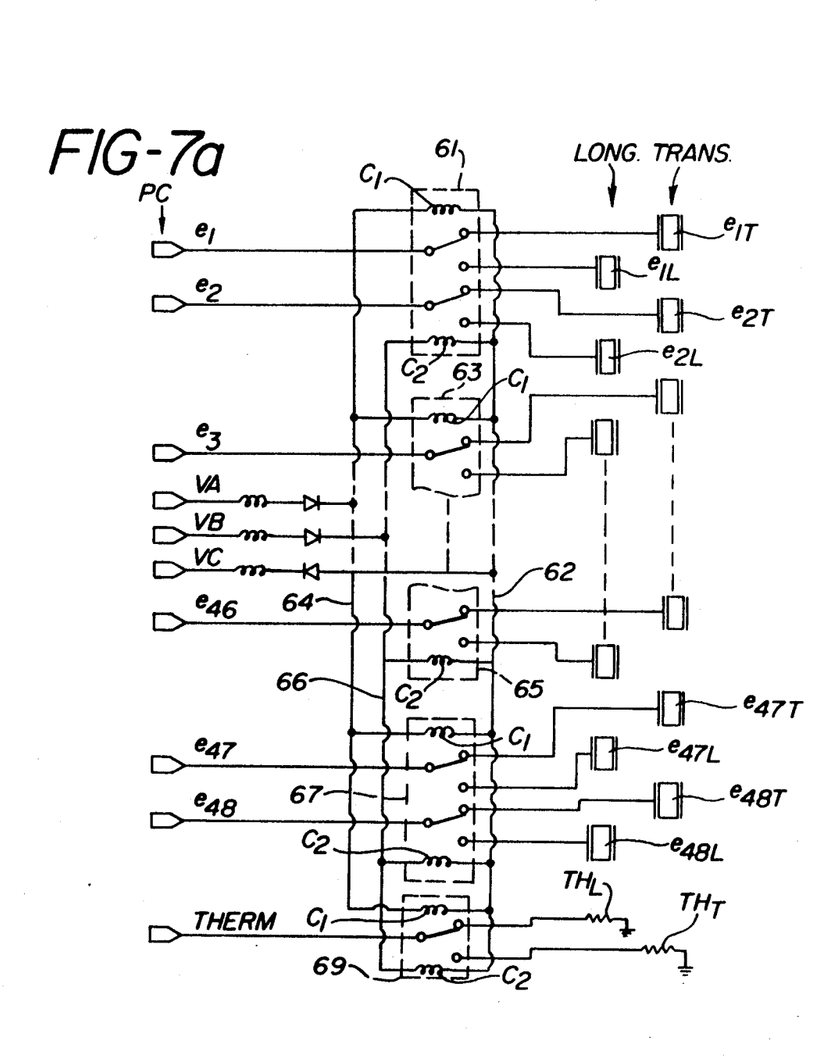
FIGS. 7a and 7b are schematic illustrations of the electronic circuitry of the scanhead of FIGS. 1-4.
Figure 7B:
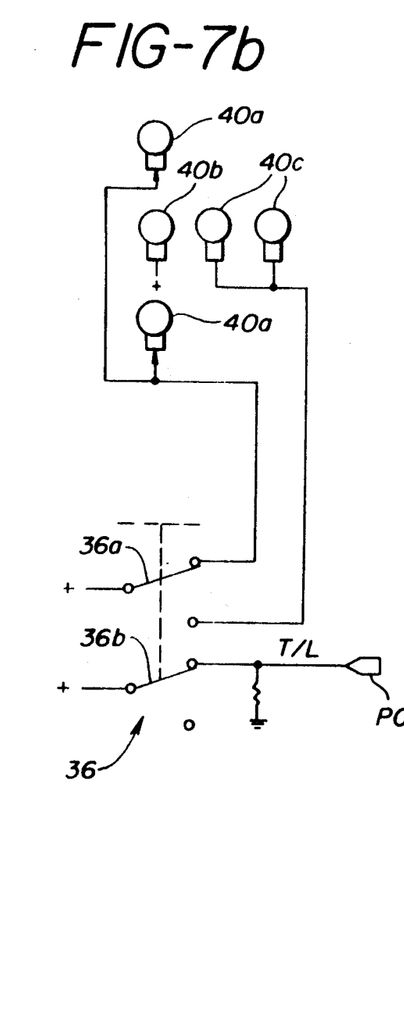

FIGS. 7a and 7b schematically illustrate the electronic circuitry of the transesophageal scanhead 10 which interacts with the ultrasonic diagnostic system through the connector pins PC. The connector pins PC are shown in the vertical column at the left of FIG. 7a and as shown in FIG. 7b, as well as the signals which are connected by way of the individual pins. In the column labelled "Trans." on the right of the schematic of FIG. 7a are shown specific elements $e_{1T}, e_{2T}, \ldots e_{47T}, e_{48T}$ of the transverse imaging transducer array 22. Adjacent this column of transducer elements is a second column labelled "Long." which indicates individual elements $e_{1L}, e_{2L}, \ldots e_{47L}, e_{48L}$ of the longitudinal imaging transducer array 26. Associated with each transducer array and in contact therewith at the distal end of the scanhead is a thermistor $TH_L$ and $TH_T$, respectively, which senses the temperature of the array during operation. The array elements and thermistors are connected by coaxial wiring extending through the probe section 12, the articulating device 16, and the cable 18 to the remaining electrical components shown schematically in FIG. 7a, which are housed within the connector 20.

The connector 20 physically houses two printed circuit board on which are mounted a number of relays which are controlled by the diagnostic system 50. In a preferred embodiment the printed circuit boards mount twenty-four pulsing relays 61, 63, ... 65, 67 which are used to connect either the forty-eight elements of the transverse array or the forty-eight elements of the longitudinal array to the diagnostic system 50. An additional pulsing relay 69 switches between the thermistors $TH_L$ and $TH_T$ of the arrays. As FIG. 7a shows, each pulsing relay includes two single pole, double throw switches which are switched in unison under control of relay coils $C_1$ and $C_2$. One side of all of the relay coils is connected to a line 62 and controlled by a signal VC. The other side of relay coils $C_1$ is connected to line 64 and controlled by a signal VA. The other side of relay coils $C_2$ is connected to line 66 and controlled by a signal VB.

FIG. 7b schematically illustrates the electrical connections of the rocker switch 36 and the LED's of the articulating device. The rocker switch 36 includes a double pole, double throw switch mechanism indicated by 36a and 36b. When switch contacts 36a are switched in the illustrated position, LED's 40a are energized by the rocker switch. When the switch contacts 36a are moved to the other switch position, LED's 40c are illuminated. The LED 40b is illuminated whenever the transesophageal scanhead is selected for use by the diagnostic system 50. The other contacts 36b of the switch mechanism apply a positive signal T/L to the diagnostic system 50 when set in the illustrated position, and a low or ground level signal T/L when set in the other position.

Figure 8:
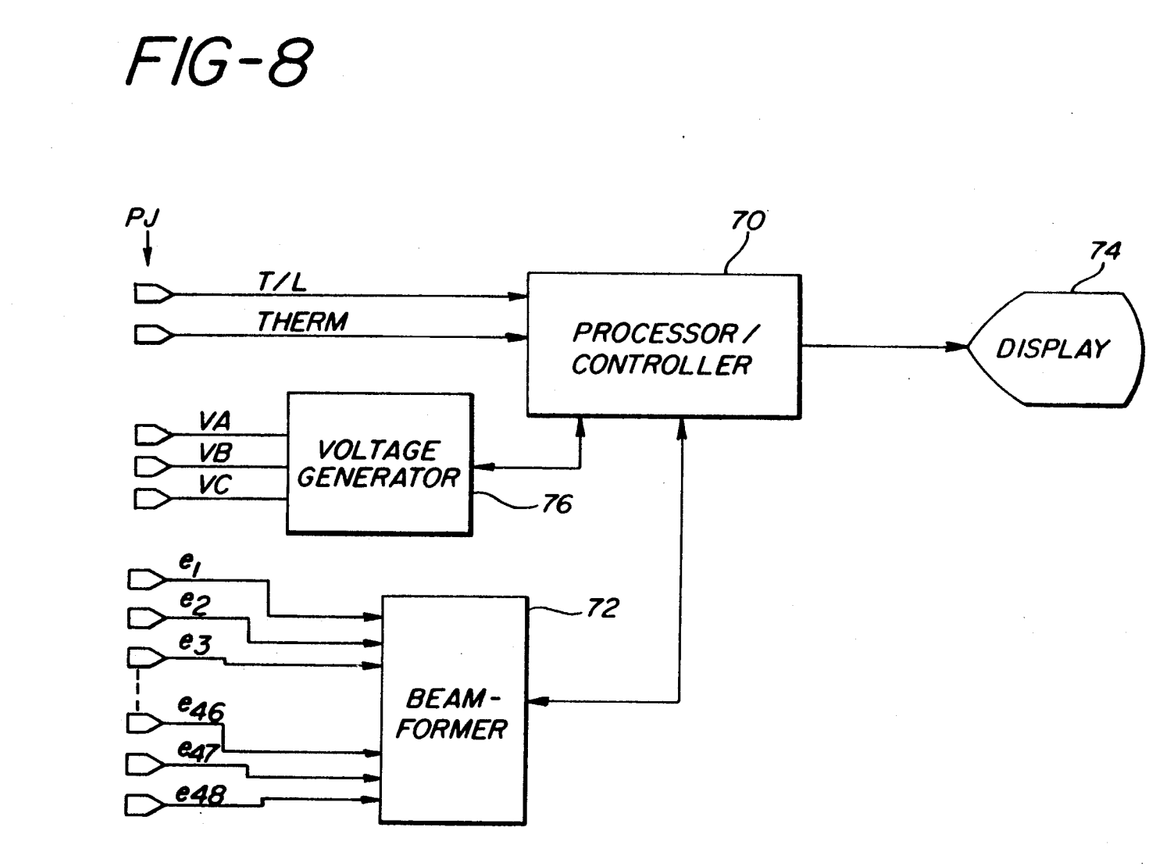
FIG. 8 is a block diagram of that portion of the ultrasonic imaging system of FIGS. 5 and 6 which interfaces with the electronic circuitry of FIGS. 7a and 7b.

FIG. 8 illustrates in block diagram form those portions of the ultrasonic diagnostic system 50 which interact with the signals shown in FIGS. 7a and 7b. To the left of the drawing are shown the pins PJ of the system jack 52. The T/L transducer array selection signal and the thermistor signal THERM are applied to a processor/controller 70. These signals are monitored by the processor/controller to provide indications of the desired image plane of the transesophageal scanhead and any overheating conditions of the transducer array. The processor/controller controls a beamformer 72 to send energizing pulses and receive echo information from the individual transducer elements of the selected transducer array. Received echo information is transferred from the beamformer 72 to the processor/controller 70 for further processing and ultimate display on an image display 74. The processor/controller also controls a voltage generator 76 to send appropriate voltage signals VA, VB, and/or VC to the transesophageal scanhead in response to a change of state of the T/L transducer array selection signal.

Operation of the ultrasonic diagnostic system 50 and the transesophageal scanhead of the present invention may be understood by concurrent reference to FIGS. 7a, 7b, and 8. When the transesophageal scanhead is plugged into the system jack and the scanhead is selected, the system examines the state of the transducer array selection signal T/L. If the rocker switch 36 is set in its forward position, the forwardmost transducer array is selected to image the transverse plane. The switch contacts 36a and 36b are then set as shown in the drawings. Contacts 36a illuminate LED's 40a which, in conjunction with LED 40b, illuminate a transverse pattern across the articulating device. The sensing of a positive T/L signal from the contacts 36b by the processor/controller 70 result in the generation of pulse signals VA and VC. These pulse signals are applied to the pulsing relay coils $C_1$, causing the relays to set in the switch positions shown in FIG. 7a. The pulsing relays thereby connect the forty-eight elements $e_{1T}$–$e_{48T}$ of the transverse imaging array and the its thermistor $TH_T$ to the system beamformer 72. The ultrasonic diagnostic system is now configured to operate the transversely oriented scanhead transducer 22 and display received echo information on the display 74.

If the clinician desires during the diagnostic procedure to switch to the longitudinal scanning mode he merely depresses the rocker switch to the rear. The switch contacts 36a, 36b now are in their alternate positions. Contacts 36a illuminate LED's 40c on the articulating device which, in concert with LED 40b, illuminate a longitudinal pattern along the articulating device. Contacts 36b are now set to apply a ground level T/L signal to the diagnostic system.

The processor/controller responds to the new state of the T/L signal by halting operation of the beamformer 72 for approximately 50 milliseconds. This prevents the transmission of energizing signals to the pulsing relays while the relays are being reset. The processor/controller generates pulse signals VB and VC, which are applied to the pulsing relay coils $C_2$. These pulse signals cause the relays to set in their alternate positions, thereby connecting the elements $e_{1L}$–$e_{48L}$ and thermistor $TH_L$ of the longitudinal array to the beamformer 72. The system and transesophageal scanhead are now configured to scan longitudinal planes using the transducer array 26.

As a further aid to the clinician, the processor/controller may also display a textual message on the image display 74 when the scanning plane is changed. For example, once the image plane has been switched from transverse to longitudinal imaging, the system may display a message such as "LONGITUDINAL IMAGE MODE" for a period of a few seconds. Thus, the selected scanning plane is confirmed visually in two ways to the clinician, periodically on the image display and continuously by the LED display on the transesophageal scanhead itself.

Figure 11:
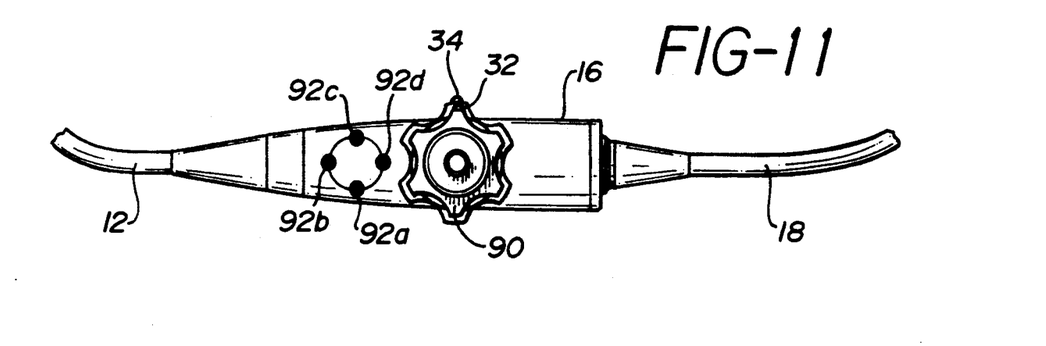
FIG. 11 illustrates a top plan view of the control unit of a multiplane transesophageal scanhead.

These concepts of the integration of the functions of image plane control, selection, and display between the ultrasonic diagnostic system 50 and the transesophageal scanhead are directly applicable to another form of transesophageal scanhead which permits image plane selection, the multiplane transesophageal scanhead. Such a scanhead is shown and described in U.S. Pat. No. 4,543,960 which is hereby incorporated by reference. In such a scanhead the image plane of an ultrasonic transducer is turned so as to enable imaging of the transverse plane, the longitudinal plane, and any plane therebetween. In fact, rotation of the plane over a full 360° is possible with such scanheads. One technique for turning the image plane is to physically turn the transducer of the scanhead as described in the '960 patent. For instance, an additional control knob 90 on the articulating device 16 as shown in FIG. 11 can be used to manipulate the control cables and pulley of the apparatus of the '960 patent to thereby rotate the transducer. Alternatively control of the motion of the transducer can be provided electronically from the diagnostic system 50. A control knob such as knob 91 on the system 50, shown in FIG. 5, can be turned to send control signals through the system jack 52 and scanhead connector 20 to an actuating mechanism in the scanhead. Such a mechanism could, for instance, be a motor and shaft inside the articulating device 16. As the motor is actuated by the control signals and its shaft turns, cables wound around the motor shaft turn the shaft on which the transducer is mounted, thereby rotating the transducer under electronic control.

Ultrasonic diagnostic systems such as that shown in FIG. 5 conventionally include a recording device as indicated at 81. The recording device could be a video cassette recorder or a hard copy printer, for instance. These devices make records of the ultrasonic images which are viewed on the system monitor 82 for later review by a diagnosing physician. However, when the system is used to make and record images from a scanhead with selectable image planes, it is desirable to provide the diagnosing physician with an indication on the recorded image of the orientation of the image plane in relation to some reference. Preferably, such indication is recorded with and appears on the recording of the image.

Figure 9:
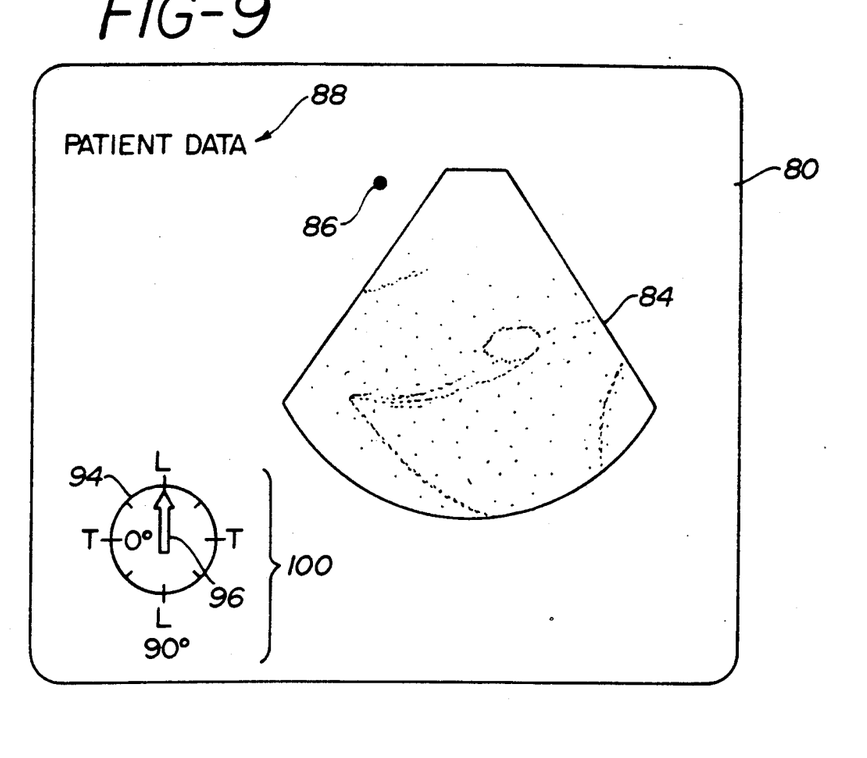
FIG. 9 illustrates an image on the monitor of the ultrasound system of FIG. 5, showing simultaneous display of an image plane and an image plane indicator.

FIG. 9 illustrates a video frame 80 which appears on monitor 82 of the ultrasonic diagnostic system when the system is used in conjunction with a multiplane transesophageal scanhead. This video frame 80 shows a representation of an ultrasonic sector image 84 of a patient's heart. To the left of the sector image 84 is a dot 86 which indicates the side of the image at which transducer element #1 is located. In this illustration the transducer would be located horizontally along the top of the sector image 84 with element #1 of the transducer array being at the left side. The dot, in effect, provides and indication of the left-right orientation of the transducer array and image.

In the upper left corner of the video frame 80 is alphanumeric patient data as shown at 88. In the lower left corner of the frame are two indications 100 of the orientation of the ultrasonic image plane, one graphic and one numeric. The graphic indicator includes a circle 94 and an arrow 96. As the control knob 90 or 91 for the image plane is turned it turns the shaft of a potentiometer which sends a variable voltage to the processor/controller 70 of the system 50. With the variable voltage being representative of the turning of the knob and hence the selected image plane, the processor/controller is able to generate a graphical arrow 96 for display at a corresponding angle in the circle 94. In the example of FIG. 9, the arrow is pointing directly upward and at a letter "L", indicating that the sector 84 is displaying a longitudinal image plane of the heart. For convenience, "longitudinal" is taken in this example to also mean in alignment with the longitudinal axis of the probe section 12 of the scanhead. The head of the arrow 96 also indicates the direction of the dot 86, so that this example would tell the diagnosing physician that he or she is viewing a longitudinal cross-section of the heart and that element #1 of the transducer array is oriented toward the top of the heart. As a precise numeric indication of image plane orientation, the indicator 100 also shows that the image plane 84 is at a 90° angle in relation to the zero degree reference, which is a transverse orientation with the dot 86 and element #1 to the left. The 90° number is simply derived by the processor/controller 70 by a measure (e.g., by means of an analog to digital converter) of the orientation-proportionate variable voltage supplied by the potentiometer of the control knob 90, 91 and a table look-up. In FIG. 9, the two transverse plane are marked with a "T" and the two longitudinal planes are marked with an "L" to denote these as planes of specific reference.

Other graphic indicators will occur to one skilled in the art, such as a fan-shaped pictograph of an image sector which rotates with rotation of the image plane.

Figure 10:
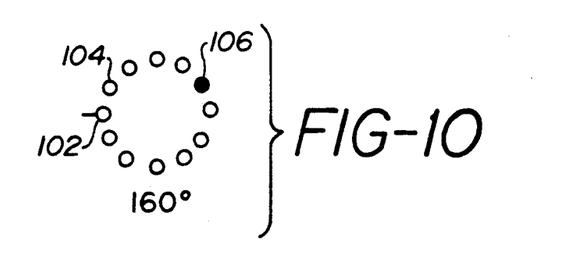
FIG. 10 illustrates an alternate image plane indicator for use in conjunction with a selected and displayed image plane.

FIG. 10 shows an alternate form of the indicator 100 of FIG. 9. In this embodiment the circle 94 and arrow 96 of FIG. 9 are replaced with a circle of dots which fill in or light up in correspondence with the selected image plane orientation. In this example the dot 102 is the reference dot for the transverse plane and the dots continue approximately every 30° around the circle. Dot 106 is filled in, providing a graphic indication that the image plane is oriented at approximately a 150° angle in relation to the reference transverse plane or transverse orientation to the axis of the probe section 12. The number below the circle of dots shows that the exact angle of orientation is 160° in relation to the reference transverse plane or axis.

As noted above, the longitudinal and transverse plane orientations are of special significance and are preferred for use as references. It is further desirable to enable the user of a multiplane transesophageal scanhead to readily orient the scanhead to one of these planes. One preferred approach is to detent the control knob 90 or 91 to "click" into position at these locations as the knob is turned. In addition to the tactile indication provided by the detented knob, a visual marker on the scanhead articulating device 16 can be used, consistent with the principles of the embodiment of FIG. 4. In the embodiment of FIG. 11, four LED's 92a, 92b, 92c, and 92d are arranged in a circle next to the control knob 90. Whenever the control knob is turned to align the transducer in one of the four transverse or longitudinal scan planes, the appropriate one of the four LED's is illuminated. For instance, the illumination of LED 92b would indicate that the image plane is aligned with the longitudinal plane of the heart (or scanhead) with element #1 of the transducer array located toward the bottom of the heart. The LED's could be illuminated in response to specific sensed levels of the variable potentiometer voltage mentioned above, or in response to the closure of switches at the detent positions of the control knob. In either case the user would be able to view the articulating device 16 while turning the control knob for plane selection and for simultaneous indication that one of the four reference planes has been located.

What is claimed is:

1. An ultrasonic diagnostic system for providing ultrasonic diagnostic information from the interior of a body comprising:
   a transesophageal scanhead comprising:
      probe means for insertion into the body for scanning in one of a plurality of selectable scanning plane orientations in relation to an axis of said scanhead;
      means adapted to be located external to the body during use of the transesophageal scanhead for manipulating said probe means; and
      means, coupled to said probe means, and actuated by a user, for selecting a desired scanning plane orientation; and
   an operating and control system comprising:
      means for operatively connecting said transesophageal scanhead to said operating and control system;
      means, responsive to said probe means, for displaying an ultrasonic image in a selected scanning plane orientation; and
      means, responsive to the selection of a scanning plane orientation by said desired scanning plane orientation selecting means, and coupled to said displaying means, for simultaneously displaying on a common display a) an indication of the selected scanning plane orientation in relation to a predetermined reference orientation and b) said ultrasonic image.

2. The ultrasonic diagnostic system of claim 1, wherein said ultrasonic image displaying means comprises a video monitor, and wherein said simultaneously displaying means comprises means for indicating said selected scanning plane orientation on said monitor.

3. The ultrasonic diagnostic system of claim 2, further comprising a recording device for recording a video image frame which includes said ultrasonic image and said selected scanning plane orientation indication.

4. The ultrasonic diagnostic system of claim 1, wherein said desired scanning plane orientation selecting means is attached to said manipulating means.

5. The ultrasonic diagnostic system of claim 1, wherein said simultaneously displaying means comprises means for providing a graphical indication of said selected scanning plane orientation.

6. The ultrasonic diagnostic system of claim 5, wherein said simultaneously displaying means further comprises means for providing a reference indication of a predetermined scanning plane orientation.

7. The ultrasonic diagnostic system of claim 6, wherein said reference indication comprises means for indicating the degree of transverse or longitudinal orientation of the scanning plane with reference to an axis of said probe means or the body.

8. The ultrasonic diagnostic system of claim 5, wherein said graphical indication comprises a circle and a pointer to a specific point around said circle.

9. The ultrasonic diagnostic system of claim 1, wherein said reference orientation comprises alignment with a longitudinal or transverse plane of the body.

10. The ultrasonic diagnostic system of claim 1, wherein said reference orientation comprises alignment with the longitudinal axis of said probe means.

11. The ultrasonic diagnostic system of claim 1, wherein said reference orientation comprises alignment with a transverse plane of the heart.

12. An ultrasonic diagnostic system for providing ultrasonic diagnostic information from the interior of a body comprising:
- a scanhead including:
  - probe means for insertion into the body for scanning in one of a plurality of selectable scanning plane orientations in relation to an axis of said scanhead;
  - means adapted to be located external to the body during use of the scanhead for manipulating said probe means; and
  - means for connecting sand scanhead to an operating and control system;
- an operating and control system, including
  - means for connecting with said scanhead connecting means;
  - display means, responsive to said probe means, for producing an ultrasonic image in a selected scanning plane orientation; and
  - means responsive to the selection of a given scanning plane orientation for simultaneously displaying on said display means an indication, in relation to a reference scanning plane orientation, of the selected scanning plane orientation and said ultrasonic image; and
- means, coupled to said scanhead and said simultaneously displaying means for controlling the selection of said scanning plane orientation and said indication of the selected scanning plane orientation,
- wherein said simultaneously displaying means comprises means for displaying a numerical indication of said selected scanning plane orientation.

13. The ultrasonic diagnostic system of claim 12, wherein said numerical indication is calibrated in degrees of a circle.

14. An ultrasonic diagnostic system for providing ultrasonic diagnostic information from the interior of a body comprising:
- a scanhead including:
  - probe means for insertion into the body for scanning in one of a plurality of selectable scanning plane orientations in relation to an axis of said scanhead;
  - means adapted to be located external to the body during use of the scanhead for manipulating said probe means; and
  - means for connecting said scanhead to an operating and control system;
- an operating and control system, including
  - means for connecting with said scanhead connecting means;
  - display means, responsive to said probe means, for producing an ultrasonic image in a selected scanning plane orientation; and
  - means responsive to the selection of a given scanning plane orientation for simultaneously displaying on said display means an indication, in relation to a reference scanning plane orientation, of the selected scanning plane orientation and said ultrasonic image; and
- means, coupled to said scanhead and said simultaneously displaying means for controlling the selection of said scanning plane orientation and said indication of the selected scanning plane orientation,
- wherein said simultaneously displaying means comprises means for displaying a graphical and a numerical indication of said selected scanning plane orientation.

15. An ultrasonic diagnostic scanhead system for providing ultrasonic diagnostic information form the interior of a body comprising:
- probe means for insertion into the body, including transducer means for scanning in one of a plurality of selectable scanning plane orientations in relation to an axis of said probe means;
- means, coupled to said probe means, for manipulating said probe means;
- means for connecting said scanhead to instrument means for processing electrical information signals produced by said transducer means;
- means, coupled to said probe means, for controlling the selection of said scanning plane orientation; and
- display means, coupled to said selection controlling means and said probe means, and responsive to the selection of a scanning plane orientation, for simultaneously displaying on a common display an indication of the scanning plane orientation in relation to a reference orientation and an ultrasonic image in said selected scanning plane orientation.

16. The ultrasonic diagnostic scanhead system of claim 15, wherein said display means is attached to said manipulating means.

17. The ultrasonic diagnostic scanhead system of claim 15, wherein said display means is attached to said instrument means.

18. The ultrasonic diagnostic scanhead system of claim 15, wherein said reference scanning plane orientation comprises a transverse or longitudinal plane with reference to an axis of said probe means or the body.

19. Ultrasonic diagnostic apparatus for providing ultrasonic diagnostic information form the interior of a body comprising:
- probe means for insertion into the body, including transducer means for scanning over a plurality of selectable scanning plane orientations in relation to an axis of said probe means;
- means for manipulating said probe means;
- means for connecting said scanhead to instrument means for processing electrical information signals produced by said transducer means; and
- means, coupled to said probe means, for controlling the selection of said scanning plane orientation, said controlling means including detent means for preferentially setting said controlling means for selection of a predetermined scanning plane orientation.

20. The ultrasonic diagnostic scanhead of claim 19, further comprising display means, coupled to said controlling means, for displaying processed electrical information signal of said transducer means and for indicating the selection of said predetermined scanning plane orientation.

21. An ultrasound diagnostic system for providing ultrasonic diagnostic information from the interior of the body comprising:
- a scanhead including a probe for insertion into the body, said probe generating ultrasound signals responsive to an applied transmit signal and receiving ultrasound signals, and generating receive signals corresponding thereto, said probe generating and receiving ultrasound signals in a direction defined by the angular orientation of said probe;

an ultrasound system operatively connected to said scanhead, said ultrasound system applying said transmit signals to said probe, receiving said receive signals from said probe, and displaying said ultrasonic diagnostic information;

probe orientation control means coupled to said probe for altering the angular orientation of said probe responsive to a probe control signal, thereby altering the direction that said probe transmits and receives ultrasound signals; and, a manually actuatable selector operatively connected to said probe orientation control means, said selector generating said probe control signal to cause said probe orientation control means to alter the angular orientation of said probe: and, a probe orientation display responsive to said probe orientation means, said display providing a visual indication of the angular orientation of said probe.

22. The system of claim 21 wherein said probe orientation display is disposed on said scanhead.

23. The probe orientation display of claim 22 wherein said probe orientation display includes light emitters arranged to approximate the different angular orientations of said probe, and wherein at least one light emitter is energized to correspond to said selected angular orientation of said probe.

24. The system of claim 21 wherein said probe orientation display is disposed on said ultrasound system.

25. The probe orientation display of claim 24 wherein said probe orientation display shows said probe angular orientation simultaneously with the display of said ultrasonic diagnostic information.

26. The probe orientation display of claim 25 wherein said probe orientation display shows said probe angular orientation on the same display that said ultrasonic diagnostic information is displayed.

27. The probe orientation display of claim 24 wherein said probe orientation display provides a graphic indication of the angular orientation of said probe.

28. The probe orientation display of claim 24 wherein said probe orientation display provides a numerical indication of the angular orientation of said probe.

29. The system of claim 21 wherein said probe includes a plurality of transducer elements, and wherein said probe orientation control means alters the angular orientation of said probe by selectively coupling said applied transmit and receive signals to said transducer elements and to said ultrasound system.

* * * * *